US008753878B2

(12) United States Patent
Kriman Fleiderman et al.

(10) Patent No.: US 8,753,878 B2
(45) Date of Patent: Jun. 17, 2014

(54) PROCESS AND FORMULATION FOR IMMUNIZING FISH IN AQUACULTURE SYSTEMS

(75) Inventors: Salomón Luis Kriman Fleiderman, Concepción (CL); Miguel Ernest Reyes Hernandez, Concepción (CL); Patricio Alejandro Oyarzun Cayo, Concepción (CL); Claudio Ricardo Alfonso Villegas Ferrari, Concepción (CL); Iván Patricio Ñancucheo Cuevas, Concepción (CL)

(73) Assignee: EWOS S.A., Concepcion (CL)

( * ) Notice: Subject to any disclaimer, the term of this patent is extended or adjusted under 35 U.S.C. 154(b) by 644 days.

(21) Appl. No.: 12/520,287

(22) PCT Filed: Dec. 20, 2007

(86) PCT No.: PCT/EC2007/000004
§ 371 (c)(1),
(2), (4) Date: Jan. 21, 2010

(87) PCT Pub. No.: WO2008/077413
PCT Pub. Date: Jul. 3, 2008

(65) Prior Publication Data
US 2011/0086087 A1 Apr. 14, 2011

(30) Foreign Application Priority Data
Dec. 22, 2006 (CL) .................................. 3676-2006

(51) Int. Cl.
*C12N 15/00* (2006.01)
*C12N 15/40* (2006.01)

(52) U.S. Cl.
USPC ...... 435/320.1; 435/455; 426/656; 424/186.1

(58) Field of Classification Search
USPC .............. 435/320.1, 455; 426/656; 424/186.1
See application file for complete search history.

(56) References Cited

PUBLICATIONS

Aranda et al., "Transfection of salmon cellular line CHSE-214 using an non-commercial liposome." Arch Med. Vet. 39, No. 2 (2007).
Boudinot et al., "Combined DNA Immunization with the Glycoprotein Gene of Viral Hemorrhagic Septicemia Virus . . . " Virology 249, 297-306 (1998).
Corbeil et al., "Nanogram quantities of a DNA vaccine protect rainbow trout fry against heterologous strains of infections . . . " Vaccine 18 (2000) 2817-2824.
Corbeil et al., "Fish DNA vaccine against infectious hematopoietic necrosis virus . . . " Fish & Shellfish Immhnology (2000) 10, 711-723.
Fernandez-Alonso et al., "A model to study fish DNA immersion vaccination by using the green fluorescent protein." Journal of Fish Diseases (1999) 22, 237-241.
Fernandez-Alonso et al., "DNA vaccination by immersion and ultrasound to trout viral haemorrhagic septicaemia virus." Vaccine 19 (2001) 3067-3075.
Garver et al., "Efficacy of an infectious hematopoietic necrosis (IHN) virus DNA vaccine in Chinook . . . salmon." Diseases of Aquatic Organisms, vol. 64: 13-22 (2005).
Kanellos et al., "The safety and longevity of DNA vaccines for fish." Immunology (1999) 96, 307-313.
Lapatra et al., "The Dose-Dependent Effect on Protection and Humoral Response to a DNA Vaccine . . . " Journal of Aquatic Animal Health 12:3, 181-188 (2000).
Lorenzen et al., "DNA Vaccination of Rainbow Trout against Viral Hemorrhagic Septicemia Virus . . . " Journal of Aquatic Animal Health 12:3, 167-180 (2000).
Lorenzen et al., "Time course study of in situ expression of antigens following DNA-vaccination against VHS in rainbow trout . . . " Fish & Shellfish Immunology 19: 27-41 (2005).
Mikalsen et al., "Protection of Atlantic salmon *Salmo salar* against infectious pancreatic necrosis after DNA vaccination." Diseases of Aquatic Organisms 60:11-20 (2004).
Perrie et al., "Liposome (Lipodine TM)-mediated DNA vaccination by the oral route." Journal of Liposome Research 12(1&2), 185-197 (2002).
Romoren et al., "Immersion delivery of plasmid DNA I. A study of the potentials of a liposomal delivery system . . . " Journal of Controlled Release 85 (2002) 203-213.
Traxler et al., "Naked DNA vaccination of Atlantic salmon *Salmo salar* against IHNV." Diseases of Aquatic Organisms 38:183-190 (1999).

*Primary Examiner* — Anne Marie S Wehbe
(74) *Attorney, Agent, or Firm* — Arnall Golden Gregory LLP (57) ABSTRACT

Process, use, method and formulation of disoxyribonucleic acid vaccine inclusion (DNA) in nutritional compositions for animal in culture, particularly in fishery systems.

16 Claims, 4 Drawing Sheets

FIG. 1

Sequence 1 (S1) 5' TAAAGAAGGCATTCAACTACGGGAGA3'
Sequence 2 (S2) 5' CCCCTTGGCTCCGAGCGTTGCT3'
Sequence 3 (S1p) 5' GAAGTCTGTCTGAAGTAGAGAGCC3'
Sequence 4 (S2p) 5' GGCTCTCTACTTCAGACAGACTTC3'

FIG. 2

Clone2

Clone1

S1
S1p
S2
S2p

Segment A IPNV
3193 bp

FIG. 3 taaagaaggcattcaactacgggagactgatctcacggaaatacgacatccagagctcaacccttcccgctggtctgtatgcactcaat
gggaccctgaacgctgccaccttcgaaggaagtctgtctgaagtagagagcctaacctacaacagcttgctgtccctaacaacaaacc
cacaggacaaggtcaacaatcaaccagtgaccaaaggaattaccgtcctgaatctaccaactgggtttgacaagccatacgtccgcct
agaggacgagacgccacagggcccccagccatgaacggagcaaggatgaggtgcacagctgccatcgcaccaaggaggtatgaa
atcgacctcccatccgaacgactgccgaccgtggccgcgactgggaccccaacaacaatttatgaggggaatgccgacatcgtgaac
tccacaacagtcaccggggacataacattccagctcaaggccgaacccgtcaatgagacacggttcgacttcattctacagttcctggg
gctggacaacgacgtccccgtggttaccgtgacaagctccacgctagtcacagcggacaactacaggggggcgtcagccaagttca
cccagtcaatcccaacagaaatgattcccaaaccaatcacacgggtcaagctggcctaccagctcaaccagcagaccgcaattgcaa
acgcagcaacgctcggagcnaagggg

Figures 6, 7:
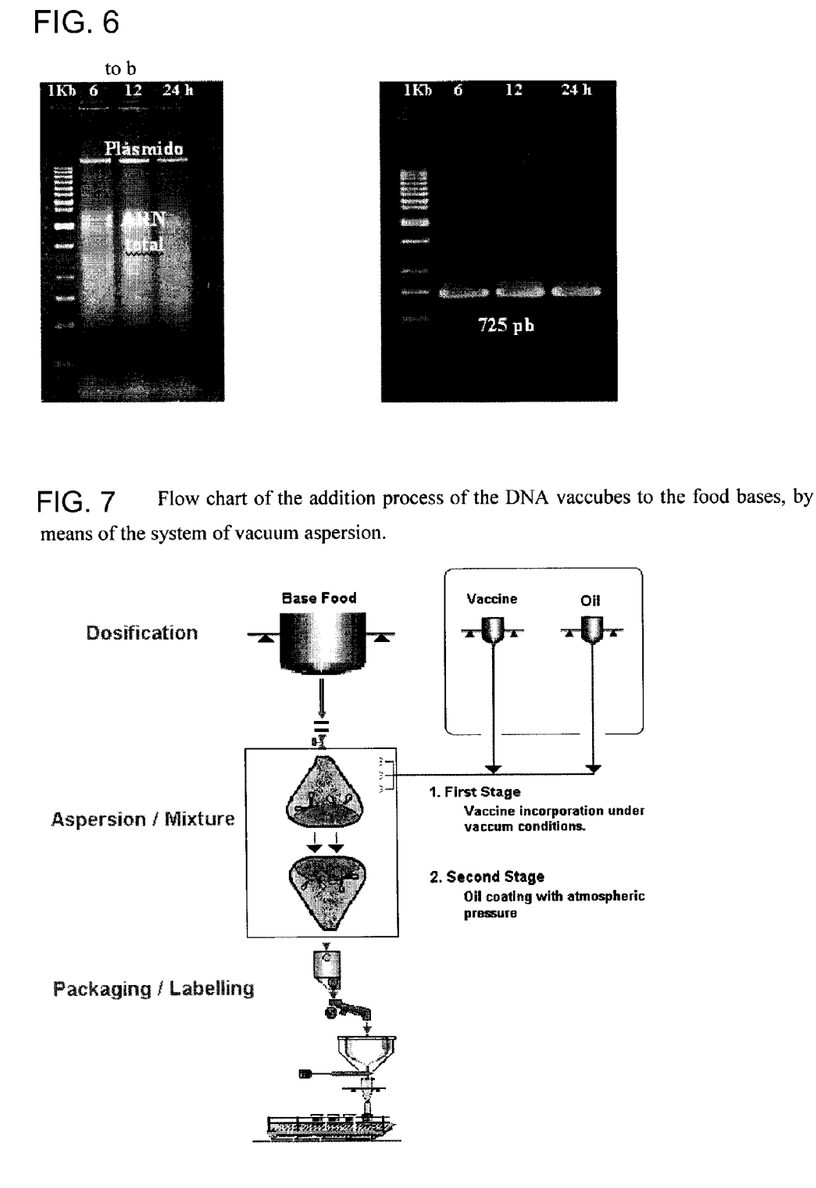
Figure 8:
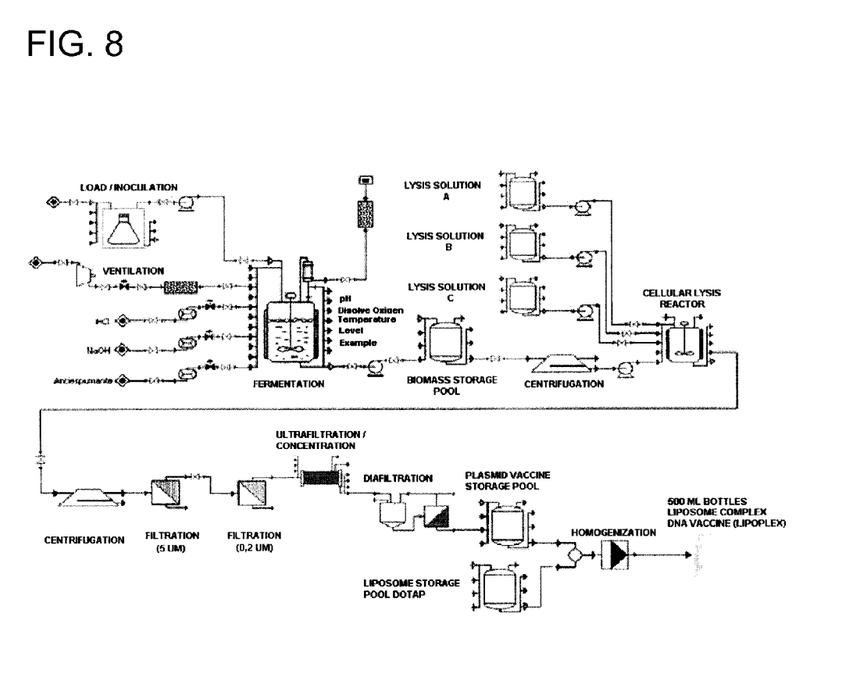

FIG. 7  Flow chart of the addition process of the DNA vaccubes to the food bases, by means of the system of vacuum aspersion.

FIG. 8

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: chemically synthesized; primer

<400> SEQUENCE: 1
taaagaaggc attcaactac gggaga                                          26

<210> SEQ ID NO 2
<211> LENGTH: 22
<212> TYPE: DNA
<213> ORGANISM: Artificial Sequence
<220> FEATURE:
<223> OTHER INFORMATION: chemically synthesized; primer

<400> SEQUENCE: 2
```

```
ccccttggct ccgagcgttg ct                                               22

<210> SEQ ID NO 3
<211> LENGTH: 24
<212> TYPE: DNA
<213> ORGANISM: Artificial Sequence
<220> FEATURE:
<223> OTHER INFORMATION: chemically synthesized; primer

<400> SEQUENCE: 3
gaagtctgtc tgaagtagag agcc                                             24

<210> SEQ ID NO 4
<211> LENGTH: 24
<212> TYPE: DNA
<213> ORGANISM: Artificial Sequence
<220> FEATURE:
<223> OTHER INFORMATION: chemically synthesized; primer

<400> SEQUENCE: 4
ggctctctac ttcagacaga cttc                                             24

<210> SEQ ID NO 5
<211> LENGTH: 724
<212> TYPE: DNA
<213> ORGANISM: Infectious pancreatic necrosis virus
<220> FEATURE:
<221> NAME/KEY: misc_feature
<222> LOCATION: (1)..(724)
<223> OTHER INFORMATION: Part of VP2 protein
<220> FEATURE:
<221> NAME/KEY: misc_feature
<222> LOCATION: (718)..(718)
<223> OTHER INFORMATION: n is a, c, g, or t

<400> SEQUENCE: 5
taaagaaggc attcaactac gggagactga tctcacggaa atacgacatc cagagctcaa      60
cccttcccgc tggtctgtat gcactcaatg ggaccctgaa cgctgccacc ttcgaaggaa     120
gtctgtctga agtagagagc ctaacctaca acagcttgct gtccctaaca acaaacccac     180
aggacaaggt caacaatcaa ccagtgacca aaggaattac cgtcctgaat ctaccaactg     240
ggtttgacaa gccatacgtc cgcctagagg acgagacgcc acagggcccc cagccatgaa     300
cggagcaagg atgaggtgca cagctgccat cgcaccaagg aggtatgaaa tcgacctccc     360
atccgaacga ctgccgaccg tggccgcgac tgggacccca acaacaattt atgaggggaa     420
tgccgacatc gtgaactcca caacagtcac cggggacata acattccagc tcaaggccga     480
acccgtcaat gagacacggt tcgacttcat tctacagttc ctggggctgg acaacgacgt     540
ccccgtggtt accgtgacaa gctccacgct agtcacagcg gacaactaca ggggggcgtc     600
agccaagttc acccagtcaa tcccaacaga aatgattccc aaaccaatca cacgggtcaa     660
gctggcctac cagctcaacc agcagaccgc aattgcaaac gcagcaacgc tcggagcnaa     720
gggg                                                                724
```

PROCESS AND FORMULATION FOR IMMUNIZING FISH IN AQUACULTURE SYSTEMS

FIELD OF THE INVENTION

The present application is in the field of immunization and nourishment compositions for animals.

The Sequence Listing submitted Dec. 15, 2010 as a text file named "25566_1_Updated_Sequence_Listing_12_15_2010.txt" created on Dec. 15, 2010, and having a size of 3 kilobytes is hereby incorporated by reference pursuant to 37 C.F.R. §1.52(e)(5).

DESCRIPTION OF THE PRIOR ART

DNA Vaccines for Fish

Within the infectious diseases that affect the fish in culture, the virus represents the greater cause of economic losses. DNA vaccines have been practiced mainly against the virus groups of: Rhabdovirus (VHSV and IHNV) and Birnavirus (IPNV).

Rhabdovirus forms the main pathogenic group of salmonidae virus group. They are ribonucleic acid virus (RNA) surrounded with an extensive complex lipid cover surrounding nucleocapside. The viral particles have cane form (rhabdo means cane) and measure around 70 nm diameter and 175 nm length (Microbiology of Brock and Madigan). Among the rhabdovirus they produce two important diseases: Viral Hemorrhagic Septicemia (VHSV) and Infectious Hematopoietic Necrosis (IHNV).

Up to date, the most successful results in DNA vaccination in the salmonidae group have been obtained against rhabdovirus: virus of Viral Hemorrhagic Septicemia (VHSV) and virus of Infectious Hematopoietic Necrosis (IHNV), which widely constitute the two viral pathologies of more worldwide impact in the culture of fish.

These DNA vaccines mainly are based on isolated plasmids of *E. coli*, for the transitory expression in eukaryotic cells. In all the cases the gene of the virus code of the viral glycoprotein is inserted pG (Anderson et al., 1996; Lorensen et al., 1998; Boudinot et al., 1998; Lorensen et al., 2000; Lorenzen et al., 2005; Lorenzen et al., 2002; McLauchlan et al., 2003; Purcell et al., 2004; Takano et al., 2004; Vesely et al., 2004).

Also using the viral glycoprotein (pG) they have been developed DNA vaccines effective for others rhabdovirus of small incidence and more restricted, as much as far as its geographic distribution as well as the species they affect, such as the Hirame rhabdovirus HIRR (Takano et al., 2004) and the Snakkehead rhabdovirus SHRV (Kim et al., 2000).

Different studies have demonstrated that these vaccines are highly effective against a variety of environmental conditions, species of salmonidae group, stages of the vital cycle of the fish and different viral stocks (Corbeil et al., 2000, Garver et al., 2005, Kurath et al., 2001, LaPatra et al., 2000, Lorenzen et al., 1999, Lorenzen et al., 2001, Traxler et al., 1999).

Experiments of dose-answers have demonstrated that the simple intramuscular injection in the rank of nanograms of plasmid DNA is enough to induce a protective immune response against Viral Hemorrhagic Septicemia (VHS) and against Infectious Hematopoietic Necrosis (IHN) in trout young rainbow (arcoiris) fishes (Corbeil et al., 2000, Lorenzen et al., 2000).

Studies accomplished with Atlantic Salmon using a codifying plasmid vaccine of complete polyprotein of the Virus of Infectious Pancreatic Necrosis (IPNV) expressed from segment A of RNA of the virus, have demonstrated that high levels of protection were obtained after their administration (Mikalsen et al., 2004). A relatively small protection has been observed when immunizing salmon coho with plasmids of high expression that contain antigenic sequences of *Psiciricketsia salmonis* (Miguel et al., 2003). On 2005 a DNA vaccine against the bacterium *Mycobacterium marine* was evaluated, on the basis of a codifying plasmid of the antigen Ag85A, which induced protection in striped bass.

Vaccine Administration Method:

The mechanism of incorporation of the DNA vaccine has constituted an important subject of investigation because of the necessity to develop methods of massive immunization that can be used in aquaculture.

The route of DNA vaccine administration that has been more effective is the intramuscular injection. Nevertheless, actually, the limitations in the size of the fish to immunize as well as the additional cost of the vaccination are problems without answer up to date.

The suitable route of administration for fish in a closed fish-farming is the bath or immersion. In this context, the routes of administration based on immersion have been evaluated in sequence to improve the practical application and massive of the DNA vaccination and to extend it to younger fishes (Corbeil et al., 2000, Fernandez-Alonso et al., 1998).

Because there is no direct DNA capture on the part of fish submerged in water that contains the dissolved naked plasmid, physics or chemical methods have evaluated themselves successful that optimize the incorporation of the plasmid vaccine by immersion, such as the use of LF ultrasound (Fernández-Alonso et al., 2001) and the hyper osmotic shock (Huising et al., 2003)

In order to induce or favor the capture of the DNA by the fish by means of immersion, at the moment methods based on the following are evaluated:

i) Complex DNA-liposomes
ii) Immersion or oral takes from microencapsulated DNA.

The cationic liposomes are submicroscopic lipid vesicles that contain phospholipids organized in bilayers, whose positive charge allows them to form complexes with the DNA loaded negatively. For this reason, mixture of synthetic as DOPE, DOTAP, DOPE: DOTAP or DOTAP: Cholesterol (Huang and Li, 1997), have become a successful alternative to transport plasmid vaccines in aquiculture (Rumoren et al., 2002).

On the matter, Fernandez-Alonso et al. (1999) they developed the first model of live monitoring the recombinant protein expression by means of vaccination by immersion of trout young rainbow fishes (0.2-0.5 g) in water being contained the complex plasmid vaccine with liposome DOTAP. In order to obtain an efficient monitoring the designed vaccine contained within its sequence the gene reporter of the green fluorescent protein (GFP), allowing the authors to quantify the emission of fluorescence in fins of great volume of the young fishes, subsequent to the treatment by immersion. The fluorescence detected between 2-3 days after exhibition with the plasmid vaccine and up to 10 days post-cure.

Recently, Rumor et al. (2004) studied the expression in different organs from a formulated plasmid vaccine with liposome. The administration of the plasmid including the marking gene of luciferase, through different routes (intraperitoneal, intramuscular, intravenous, immersion or anal), throws a greater expression of luciferase by means of use of the complex vaccine-liposome, in relation to other mechanisms of administration.

A search in the main data bases of the patent offices of the world was accomplished. This search will be classified in six fundamental parts, indicating in each case what was the criterion used. The first four searches were related to precise elements in the invention, in as much the two last searches are related to the vaccine process of manufacture and inclusion in a nutritional formulation:
1. Primers used;
2. Plasmid used;
3. Bacterial stock E. coli JM-109;
4. Liposome construction DOTAP;
5. DNA vaccines for fish;
6. Process of Formulation with DNA or other elements of interest.
1. Search Related to Primers:

The primers used in this invention correspond to two novel sequences of 22 and 26 bp

```
                                               SEQ ID NO: 1
    S1 5' 3 TAAAGAAGGCATTCAACCGGGAGA' sense (26)

SEQ ID NO: 2
    S2 5' 3 CCCCTTGGCTCCGAGCGTTGCT' antisense (22)
```

The sequences used to induce immunity in fish in the prior art is very limited. There are few applications that have protected similar initiatives. The primers used in this application correspond to two novel sequences.

Application US2003147909, of Chilean priority, discloses a procedure to purify protein CHAP, which presents immunogenic activity and was isolated from salmon coho infected with the *Piscirickettsia salmonis* bacterium. This application filed in Chile under number CL2086-01, is not related to the present application by several reasons: (a) First of all, it looks for a protection for a different pathogen; (b) then the involved sequences are different, since they derive from a different epitope; (c) the immunogenic proteins used are different; the primers are therefore diverse; (d) it does not advance either towards the use of a liposome as a device of inclusion of a molecular basic active principle, and this is the reason why it does not get a nutritional formulation that contains a device of cession of a drug of molecular nature.

Accordingly, the use and intention of the primers to generate a sequence code or a peptide with immunogenic capacity are novel.

2. Search Related to the Plasmid Used:

The commercial plasmid to clone the insert is pcDNA4/HisMax TOPO (InvitrogenTRADE-MARK, Carlsban, Calif., and the USA). In this regard, some initiatives that disclose the use of this clone vector have been found. The best example is in WO2006003100. This application protects the expression of a vector that for a glutamate receiver, for which the expression vector was used in particular pcDNA4/TO (Invitrogen TRADEMARK, Carlsbad, Calif., the USA) adding a sequence that mGluRs codifies for a member of the group of receivers of group I, the human receiver mGluRIa. WO2006003100 seeks to protect the expression induced tetracycline of the vector that it codifies for a receiver of human metabotrropic glutamate of group I. WO2006003100 also seeks to protect the host cellular line (T-(T-Rex-293), the method to recognize an agonist and other compounds that have the capacity to modulate the activity of the same receiver, as well as the use of the transgenic cells.

WO2006003100 differs to a great extent from the present application, having in common only the fact that the same clone vector is used, but in a different form. WO2006003100 seeks to protect the use of the plasmid vector for the clone of a glutamate receiver and the substances that modulate them. However, the present application described the use of the clone system of mammals in fish. On the other hand, and to greater abundance, the clone sequence does not bear any relation to receivers from mammals, but with a viral protein, being the virus a pathogen of fish.

3. Search Related to the Stock and *E. Coli* JM-109:

The stock of *E. coli* JM-109 (Promega) derived from *Escherichia coli* K-12 are widely used as host.

RU2208637 discloses the preparation of a construct to treat patients with diabetes mellitus. For this, the gene is introduced to a bacterial vector generating the new stock bacterial, which was denominated *E. coli* JM 109/pPINS07. The protected method includes an extensive protocol of the isolation of a contained recombinant protein in the bodies of inclusion. The advantages of this procedure, among others, are the reduction of the preparation time of samples with respect to the existing technologies. In addition, the associated genetic engineering to the preparation of genes for the human insulin production is complex. In RU2208637 an increase in the hybrid protein production is indicated.

It should be mentioned that in RU2208637 as well as in the present application, stock *E. coli* JM 109 has been used as host that allows to amplify plasmids, which are widely recognized in the art for the use of the stock of *E. coli*. The novel aspect of present application is the use of the amplifying stock of a viral peptide sequence pertaining to a microorganism that is guest of fish and not of humans.

On the other hand, the prior arts that could be related, without exception, claim the extraction of the product of this stock, without having to generate a pharmaceutical composition. Other initiatives exist that protect a distinctive pharmaceutical formulation. These formulations contain an active principle obtained by techniques similar to the procedure that is desired to protect, that is to say through clone techniques. Nevertheless, the majority of these prior art documents are tied to man or to fish, but they are generally vaccine of different pathogens, using different epitopes from the used in the present application. The present application went beyond the extraction from a plasmid, a protein or a hybrid polypeptide. Although the clone product was isolated, this product was treated later to generate a composition and whose active ingredient is the clone polypeptide sequence. The drug, the composition and the route of administration present unsuspected and novel advantages on existing vaccines. The sequence has not been disclosed nor recognized previously in the art, even more, the clone in bacterial stock *E. coli* JM-109 is only one stage of an ample procedure that ends by the generation of a DNA vaccine, which is contained in a liposomal vehicle and will generate replaced immunogenic against the pathogenic organisms. The liposomes serve as vehicles that carry the pharmaceutical formulation, facilitating the protection and incorporation of the active ingredient. The complex plasmid-liposome, in future lipoplex, is added to a nutritional formulation for fish in the process for food manufacture. Once administered, the food is ingested and the active principle absorbed in the luminary zone of the intestine of the white organism, soon being expressed in the zone and other tissues, having generated a protective immunological answer. These aspects not only enjoy newness in the art but also they grant to our inventive great initiative.

JP2000295994 solves the problem of the production of xylitol through molecular techniques. JP2000295994 discloses a method that includes transforming *coli* with a gene that codifies for the enzyme xylitol dehydrogenize contained in a plasmid vector. Later, the transformed microorganism acquires the capacity to generate xylitol from D-xylulosa.

JP2000295994 shows remarkable differences with the present application. Among them we can emphasize that JP2000295994 does not claim a particular line of *Escherichia coli* as it is the line JM-109 *E. coli*, but only in generic form. Also its product is for human use. Finally, the sequences, use, product, method, route, are very different from the present application.

The production of mutant stocks inhibiting the formation of plates is the problem solved by JP2000083665. The process disclosed in JP2000083665 has as aim obtaining the gene glucosyl transferase I of *Streptococcus downei*. The gene is amplified through the PCR technique, using primers of 30 pb based on gene GTF-I. The amplification generated is attached to an expression vector to soon transform bacterium *E. coli* JM-109. Later, the recombinant stock is cultivated, the enzyme is isolated and extracted glucosyl transferase from the over floating. JP2000083665 does not have relation with the present application. The process claimed in both applications offer a solution to the diverse state of technique. However, the massive generation of the gene and its isolation is a similar procedure in molecular Biology, but with a different biological conception. Consequently, the primers used are different and the culture protocol offers deep discrepancies. These prior art documents only share global aspects, such as the use of the same stock *E. coli* JM-109, but the recombinant stock obtained is another one, besides the isolated gene that does not have report as far as the sequence or the final use of this one. In JP2000083665 the invention unit is the production of an enzyme with biological activity. The present application seeks to develop a process for food manufacture for animal in captivity. The process must allow the addition of pharmaceutically active substances. All the substances are produced through recombinant DNA techniques.

JP2000050869 discloses the obtaining of a new plasmid with capacity of autonomic replication in *E. coli*, specifically, *E. coli* JM-109. This plasmid is useful to be used as specific vector of the *Gluconobacter* sort sp. The vector was isolated from the *Glucobacter* stock oxydans IFO 3171. JP2000050869 does not bear any relation the present application, in spite of being disclosed the use of the stock of *E. coli* JM- in the descriptive memory, the bacterial sort and its use is claimed broadly speaking the Japanese proposal and only in generic form, without a stock in particular that plasmid constructs. The use of the stock in the present application is at specific level stock *E. coli* JM-109, the one that is used in the stage of massive production of the plasmid, but is a stage within the stages of the global process that is desired to claim. The nucleotides sequences as well as the concept, use and process do not bear any relation to JP2000050869.

RU2143492 discloses the development of a new recombinant plasmid that expresses the peptide leader which is united to the dominion IgG—of the proinsulin "A", system cloned at human level, the plasmid generated in the Russian document is pRRproins. The proinsulin is prepared by a procedure that involves the culture of the stock of *E. coli* JM-109—pRRproins (recombinant stock). Later is must appeal to the isolation of the bodies of inclusion, solubilization, ion-exchange chromatography, proteolysis with tripsin and other enzymes, to secure the insulin isolation. As for all applications/patents previously discussed, RU2143492 the unique characteristic that shares with the present application is the use of stock *E. coli* and the transformation with a plasmid to generate a product. That is to say, it uses the stock as vector, aspect widely conceived in the state of the technique. Nevertheless, the use is always related human genes and not as the present application that wishes to use it to clone proteins that will be expressed in animals. In addition, the sequences involved, the baits and the use are very different. In all the documents of prior art, the invention unit only subscribes to the culture of the stock transformed by a plasmid or another vector and to the isolation of the product, under different protocols. The scope in the present application is considerably wider, since a stage of the process is the clonation, through the bacterial stock, but whose plasmid carries investigation for a viral protein (VP2) of the pathogen that attacks fish. Later, the plasmid that contains the cloned sequence is isolated, to the encapsulation in a cationic liposome. This complex (liposome-plasmid) will serve as vehicle of transfer and pharmaceutical formulation for the administration of active ingredients to animals in culture. In addition, through an industrial process a completely novel technology has been developed and inventive that includes providing the vaccine in the form of food ration, since this vaccine has been included in the food. These aspects are not considered, alone or as a whole, in any of the documents in the art.

RU2130071 discloses a method of preparing hirudin HV1. The process is carried out by means of the transformation of a recombination stock of *E. coli* JM-109 (BP-32266) with a secretion vector pMTS HV1 or pMKS HV1. Once the stock was transformed, it was cultivated and soon the final items were isolated from the culture area or the periplasmic space. The constructed plasmid contains three main elements: a DNA fragment that codifies for phosphatase alkaline, hirudine fragment HV1 combined with the Accl site and the gene that determines the resistance to the ampicilline as genetic marker. The system shows as improvement the decrease of hemorrhages due to his use. RU2130071 presents several and important differences with the present application, since the gene cloned do not present similarity with the gene that is desired to amplify in the bacterium. In the present application, even though the bacterial stock is the same, neither the plasmid nor the gene present similarities, although the intention by definition is the same that it is a clonation vector. We must consider that the clonation is only a stage within the process that is desired to protect, which is not small, if considered that it is desired to claim a process of multiple stages. As all the previous documents, RU2130071 has another biological function and they only claim the bacterial stock transformed from stock *E. coli* JM-109 as host of the plasmid and a process of related isolation. In both cases it is different the use and concept from the ones used in the present application.

JP2084195 discloses a process for the protein production in big quantities. The process is based on the transformation of host microorganisms of a vector that has the particularity to take built-in the plasmid of a DNA fragment that codifies a hepatic protein. In order to initiate the process the liver is macerated and it is treated directly with enzymes. The codifying segments of human polypoprotein (HAPE) or similar to HAPE are isolated by traditional techniques. Then, the DNA of *E. coli* is treated with restriction enzymes, obtaining a sequence or codons of signal for both DNA. Once obtained the codons a structure of tandem form, all together with an expression vector is generated. The vector presents the peculiarity of a promotional TAC and a of union to ribosomes. Obtained constructo pOFAapoE, becomes a bacterial stock by incorporation of these components. For example, the stock and *coli* JM-109, which in transforming conditions produces the human E polypotrotein. The protein is excreted in the area in which the microorganism is cultivated JP2084195 presents several differences with the present application. For example, the cloned gene does not similarity with the gene that is desired to clone in the bacterium vector in the present application, since it is not human, although the bacterial stock is the same, neither the plasmid nor the gene present similarities, inasmuch as from the biological point of to use the same clone vector, but with different gene cloned, it represents a complete difference, even though the intention in this stage is the same, that is the use of a cloning vector. Therefore, the difference in the nucleotide use of the plasmid and its sequences subsists.

Although in JP2084195 the stock of *E. coli* JM-109 is used as a vector, the sequences used that is desired to claim are not human, not thus all the analyzed petitions. In addition, the clone is a stage common to all the petitions—of the of the prior art, which means to use the bacterial stock as vector is an aspect widely known in the state of the technique, but the use always is related to human and nonanimal genes. In addition, the sequence involved, the primers and the use are considerably different, inasmuch as in all of the documents of the prior art only subscribes to the culture of the stock transformed by a plasmid or another DNA vector and later isolation of the product under different protocols. The present application is much more ample, since a stage of the process that is desired to claim is the cloning of viral epitope (epitonic) through a host bacterium. The peptide sequence that is desired to clone is a polypeptide of 724 bp, which is part of protein VP2 of a viral pathogen, virus IPNV that attacks fish. The bacterium is transformed with the plasmid that contains the sequence to clone, then is worked and finally is treated to extract the plasmid, which after the purification will be encapsulated in a cationic liposome. This not used in any of the documents previously discussed. This lipoplex complex (liposome-plasmid) will serve as vehicle of an DNA sequence with a generation capacity of immune response in fish. To apply this technology to immunize fish is one application of the technology. The important aspect of the present application, as novel and completely inventive technology, is that by means of this it will be possible to provide drugs to fish and other organisms in the form of food ration, aspects that none of documents in the art consider alone or as a whole.

4. Search Related to the Use of the DOTAP Liposome:

Liposome DOTAP was used in the present application as a vehicle of transference and in addition as a complex and stabilizing element. Next the most important initiatives are discussed.

WO9807408 protects the use of the cationic liposomes that has been developed as a system of delivery or transfer for biologically active reagents. The structure of the liposome contemplates one or more substances or active agents interned between two liposomes bilamelars. This structure protects the agent in its interior. The system presents high efficiency in the "live" transfer. The highest expression of the polypeptide was obtained in the stomach, whereas the expression in several organs and tissues is increased. The referenced application claims the production of the liposome by means of heat, later addition of a cholesterol molecule, sonic, extrusion of lipids component in sequential form through filter of reduced porosity. Although WO9807408 claims the use of liposomes as molecule vehicles, it does so in generic form. In addition, the use that is granted to liposomes in this initiative is associated to cholesterol molecules, which would be collaborating. In the present application the complex formulation does not use cholesterol in its formulation nor collaborating, the sequences are novel and the use is distinctive. In the present application, the complex generation is an inserted stage in a global process. The preparation is denominated lipoplex, which does not contain cholesterol and whose sequence codifies for epitope of a viral protein. The present application is not conceived as a biological activity per se, as all the initiatives that will be discussed in point 4. Unlike all the documents of the prior art in this point, the invented formulation is different, because the liposome is a vehicle that is oriented to the expression of a sequence that will generate an answer in the immune system of fish, no applications in humans of cosmetic and/or pharmaceutical type.

WO9810748 protects a method of cationic liposomes use and the manufacture procedure. The method of use is based on the dehydration technology and rehydration of them. For this, in the first place cells are due to be collected in the morning, which are cultivated and later transferred outside the organism where it is hoped that they have therapeutic action. Then, they are introduced to the organism so that they have "live" action. WO9810748 claims the content of liposomes as codifying polynucleotides for a polypeptide. The information introduced to the liposome is double DNA fiber or mRNA, whose function is to produce an immune response in the individuals where they are administered. WO9810748 claims the polynucleotide, particularly its genetic structure, thus this must optionally present a promotional sequence and joint sequences to ribosomes. In addition, the cationic component of the liposome is glyceride. The liposomes manufacture procedure is claimed like a process that includes a series of stages that are summarized as follows: A stage of dehydration followed of a rehydration stage to generate then a micro flow and extrusion. Finally, WO9810748 claims the route of administration of the complex liposome-polynucleotide, which can be by intramuscular route, subcutaneous, intravenous or intraperitoneal with "pharmaceutically acceptable" excipients.

In WO9810748 there are deep differences with the present application, which includes the manufacture procedure of the complex liposome-nucleotide, as well as the substantial differences in the use and application of liposomes, although the global concept in the use of liposomes is the same. The procedure shows several differences. Among them it is emphasized the liposome use to generate immune "life" response without need of extracting cells of the individual, which are not claimed nor disclosed by some similar initiative, and are not present either in WO9810748, whose initiative clearly claims a procedure that implies the extraction of cells that must be worked and soon transferred. Then, by means of some sophisticated method they are reincorporated to the individual, where they will generate the therapeutic action. Still more is the inventiveness related to the present application, because the procedure that is desired to protect in the present formulation does not use collaborating, and the administration route is different from the claimed one in, WO9810748, discrepancies that emphasize the novelty and inventiveness of the present application.

US2005249794 discloses several types of liposomes, among which is liposome DOTAP. US2005249794 claims the liposome use that encapsulates oligonucleotides. These substances have the function to stimulate the secretion of cytokines. The oligonucleotides do not improve the immune response in treated mammals. Nevertheless, US2005249794 does not establish the nature of the used oligonucleotides, a specific sequence to either generate an immune response in the white organisms. US2005249794 discloses the generation of the specific immune response to antigens claimed in it, since the administration of an antigen molecule in association with lipid particles are responsible of this answer. An important aspect of US2005249794 is related to the claimed sequences, since the claimed composition contains a sequence no specified in the oligonucleotides US2005249794 indicates that the nucleic acid of the oligonucleotide can contain a cationic lipid. Nevertheless, this must be phosphodiester or phosphotiolate. This can be or not a complementary sequence to the human genome, containing a reason as CpG, or can contain a palindrome sequence, which is a generalization by functionality.

US2005249794 describes a formulation that contains oligonucleotide with a CpG reason whose residues are united to phosphodiester and a collaborating lipid. The lipid presents a structure type PEG or PAO or ganglioside. This composition is contained in a liposome. US2005249794 claims a series of liposomes that can be used to yield the formulation, among them is the DOTAP. In the present application was only used liposome DOTAP plus the nucleotide, but this nucleotide codifies for a viral peptide, which is guest of salmon group and whose expression takes place in enteric cells. In all the initiatives that we have studied the liposome is introduced directly to the white organism. Nevertheless, the great difference of the present application is that the liposome is incorporated to a formulation to generate fish food, according to a protocol well defined. No similar document of the prior art mentions that the liposome is used in fish, since liposome DOTAP is conceived for the human use, not in all the mammals. Even so initiatives exist that claim their use in superior mammalian systems, but no initiative relates the process of food manufacture—in generic form to the introduction of substances that can be absorbed through enteric cession to other organisms different from the humans.

The method described in US2003220284 is related to a composition that uses liposome DOTAP, cholesterol and a molecule of viral nucleotide. The nucleotide is circular DNA of a recombinant adenovirus. This formulation is a therapeutic carrier to neutralize the immune response against the human gastric cancer. US2003220284 presents big differences from the present application as the formulation, method, procedure and use are different.

The procedure for the transfer of tumor like cells with nonviral vectors and later irradiation is described in Spanish ES2224836. The liposome used is DOTAP and the irradiation stage is subsequent to the use of this vector. The expressions of the transferred cells generate the factor of growth of colonies of granulocytes (GM-CSF). The use of the transferred cells in the field of the gene therapy and its use as anti-tumor medicine.

ES2224836 presents concept differences with our initiatives. For example, in the formulation process as well as in the use of the invented technology they exhibit differences at macromolecular level. Both initiatives have common solely the liposome use as transfer vector, but the plasmid as well as the information and the methodology used present deep differences, use and intention.

A method to determine the regression or progression of the cancer in a patient is in US2002168662. The procedure is based on the detection and identification of the Sp17 molecule as an antigenic test. For this, a sample of the patient previously diagnosed with cancer is practiced. In the sample the level of expression of a nucleic acid molecule is determined that codifies for the Sp17 protein. Then, the level of normal expression is compared with the level of expression of the Sp17 molecule in the patient. The variation among them will indicate the progression or regression of the cancer.

The procedure as well as the concept of the invention presents severe differences with the present application. The divergences will not be discussed since they are remote to the field of the invention, being an inventive unit completely different WO9527508 discloses a composition to generate an immune response in mammals to a certain antigen. The composition includes the antigen catched in a liposome (DOTAP) and integrated with a collaborating one ISCOM (TRADEMARK). The composition can be administered by several routes, including intranasal, intratracheal, oral, intradermal, rectal, and by means of douche. The antigen is derived from an organism involved in an infection of the skin, respiratory tract, genitourinary tract or another mucous surface. In addition the microorganism can be virus, bacterium, micoplasma or fungus. WO9527508 extends the invention field, not defining the pathogen which it can attack or the used sequences. It does not define the route of administration nor a formulation. It only defines the final function of a supposed composition that uses as a vehicle liposome DOTAP. Nevertheless, WO9527508 defines as active principle the same antigen, not the sequences that the antigen would possibly produce. In addition the composition disclosed in WO9527508 must incorporate the use of ISCOM (TRADEMARK) as collaborating. The differences are important, first in the composition, since the present application implies that the active principle is not the same antigen including in the formulation, but a sequence that generates a part of the molecule, the one that is being expressed in diverse tissues will as well generate an immune response against the pathogenic agent, fundamental difference in biological terms.

It should be noted that the complex DOTAP-nucleotide of the formulation described by the present application, is not only one stage of the process, but, rather, a vehicle of encapsulation of a novel nutritional formulation. Unlike all documents of prior art, which are related to the use of DOTAP, all claim the direct use of the pharmaceutical complex. This means that the complex together with the collaborating generate the answer under diverse methods, the biological activity is direct, then the complex active liposome-principle is used. In the documents of the prior art discussed the liposome-molecule complex and collaborating (all collaborating claims) have the same biological function, and still more important, biological activity. Only some documents of the prior art claim the generation of immune response in the white organism, generally immune response against cancer. Nevertheless, the procedures the uses derived from each formulation are different; consequently they are claimed as part of the method and in the procedure. In both cases, procedure and/or use, differences persist, since the present application is different from all because of the concept used, since it does not present direct biological activity and the protocol applied although similar elements are used, for the use of the cession vector, for example, the sequences used in the present invention are not human unlike all documents of the prior art previously set out. In other words, the active ingredient of formulation is different. In addition, the process that is desired to claim is different, when including the vehicle of cession (liposome-DNA) in a nutritional formulation animals. The first difference is in the nature of the sequences used. Secondly, the intention of the use of the plasmid. In the third place, the use of the bacterial stock to transform it with a plasmid not disclosed before into the art for the transformation and donation in this stock, and then, to introduce the plasmid in a vehicle, that although it widely conceived in the state of the technique like in the use of the plasmid as vehicle for gene therapy in men, the present application is disclosing a novel use, the use of vehicle plus an DNA sequence as vaccine for animal immunization. Aside from the previously five enunciated products, the process is recoverable by the use of the liposome, but the use in fish under this is novel. This complex, liposome-plasmid will serve as vehicle that contains in its interior a DNA vaccine and that, in addition, based on a novel and completely unsuspected technology will be provided to fish in the of food ration, aspects that none of the documents in the art considers alone or as a whole.

This application offers great advantages on the traditional vaccination systems. This application discloses a vaccine that is safe, since the reversion problem does not exist, such as vaccines of attenuated microorganisms. It does not have noxious side effects, as it happens with some collaborating ones. An effective protection against the challenge of virulent pathogenic stocks has been demonstrated, besides having great stability for the form of administration and vehicle of cession. The application is conceived as to present a long term protection.

5. Search of Documents Related to the Vaccine Preparation for Fish:

GB2308367 discloses the use of a protein that presents immunosuppressant activity. The protein was isolated from *Aeromonas* sp. It is of nonhaemolytic nature, characterized by a molecular weight of 30 KDa and it does not present enzymatic activity. The protein presents the peculiarity that suppresses the cellular immune response and can be used in vaccine formulations, especially to immunize fish, particularly salmon group against furunculous. The differences with the present application are basic as far as the concept used, and ample in relation to the manufacture process. First of all, GB2308367 does not mention the route of administration, or the final composition of the vaccine. It only mentions the objective and that "it can be used in vaccine formulations or for fish". In no case GB2308367 mentions how or the form of vaccination of the fish or the specific formulation for it, the route is completely ignored in GB2308367. It is different from the present application, which specifically looks for the objective of protection of a process, contemplates the defense of novel stages, which present unsuspected advantages in them. In addition the existing process is novel. Additionally, each stage in particular presents exceptional products. One of the final products is the vaccine for fish, whose formulation, mechanism of cession, route and formulation is obviously separate from the unit of invention of GB2308367.

U.S. Pat. No. 5,939,073 discloses the isolation of a viral stock that produces pancreatic diseases in fish. The vaccine presents as active ingredient the inactivated virus. In addition the kit of associate diagnosis is protected. The diagnosis is based on finding an antibody that detects the specific form of the virus of the sample of the evaluated fish. The antibody has a detectable marker. The method includes taking a sample of the fish, the reaction with a reagent and later detection of the amount of virus in the sample. The patent claims other procedures related to the viral detection of specific tissues. The differences are large. First, U.S. Pat. No. 5,939,073 uses attenuated virus and not nucleic acid sequences. The vaccine does not have effect for the same virus (IPNV). The present application a specific formulation for the pathogen is described. U.S. Pat. No. 5,939,073 does not use or mentions plasmids, stocks or liposomes and its cession is not tied to a nutritional formulation for the virus that is desired to protect.

U.S. Pat. No. 5,914,260 describes a new virus that causes fish pancreatic disease, particularly in Atlantic salmon. The method of isolation of the virus is disclosed, also the use of the viral stock or the proteins and/or polypeptides derived such as vaccines.

The diagnosis kit is disclosed but not protected. Only the viral stock is claimed. The differences with the present application are large including the method, use, and procedures.

A vaccine against the virus of the infectious anemia of the salmon (USA) is disclosed under the Norway priority and WO0072878. The invention is related to the development of a vaccine against the ISA virus, which is developed as viral DNA sequences which codify isolate immunogenic proteins from viral capside. The diagnosis kit for the detection of viral nucleic acid sequences is also disclosed. The vaccine is characterized to include an DNA sequence that codifies for a viral protein. The differences with the present application are large. WO0072878 does not present the same sequences or similar functionality. In addition, the plasmid used to clone the sequence does not present any relation with the one used in the present application. Finally, WO0072878 did not use liposome nor describes some formulation. The process is outside the inventive field, since it is not mentioned in WO0072878.

European EP1094069 describes a formulation, whose main element is a nucleic acid sequence that codifies for a structural protein of the virus. The microorganism studied was the virus of salmon infectious anemia. The protein isolation (SP-1), the use for the diagnosis or vaccine intentions and reagents are claimed in EP1094069. The composition of the vaccine is simple, includes the sequence of nucleic acid or protein plus "acceptable" carrier. The kit is claimed for diagnosis. The principle is based on classic immunological aspects; the antibodies that recognize this protein (SP1) detect a nucleic acid or a protein (SP-1) in the sample. The differences with the present application are extensive from the sequence, the donation vector, the vehicle or carrier, the presence of plasmid and liposomes in the pharmaceutical formulation. The integrity of the vaccine in the manufacture process is affected neither in the novelty nor in the inventive level by the prior art previously discussed.

US2005164176 and US20055261227 disclose the use of diverse sequences of nucleic acids or peptides for the vaccine preparation and immunization of fish against ISA virus. The vaccines are based on the fact that the synthesized sequences are from the virus or in analogous form, the sequences are translated to a peptide. The peptide is part of the vaccine, since in US2005164176 and US20055261227 the criterion applied is that the proteins are the generating surface of viral antigenic Therefore, in both cases, the use of a vaccine against ISAV is disclosed, and the incorporation of a specific peptic sequence in a vaccine is protected by both In addition, the vaccine is protected as a pharmaceutics form, as well as the kit of diagnosis and the cell that contains the composition (transforming). The differences with the present application are large, from the sequences, the vector, the plasmid and the organism used. The aspects shared only refer to the concept of a DNA vaccine or polynucleotide included, but even so important differences persist as the vehicle of transformation or cession or the same formulation is deeply divergent. Another different aspect which is not less important is the intention, diverse to the intention conceived in the present application.

US2005226895 discloses the generation of immunity against *Piscirickettsia salmonis*, in salmonidae group, through a pharmaceutical formulation that contemplates the nucleotide or peptide sequences as active principle and a carrier, as in US2005164176 and US20055261227, which disclose the same concept, except for the reservation of the sequences. The present application, apart from the differences regarding the sequences, the cession and formulation, presents differences in the microorganism, donation vector, the use of a plasmid that has been used mainly to clone DNA of humans and not of animals, and to introduce the formulation in a carrier of transfer such as the cationic liposome DOTAP. The differences referring to the manufacture food process that will contain the plasmid vaccine persist.

US200423580 discloses a vaccine against ISAV. Antigenic polypeptides or nucleic acid molecules were put in a refuge that codify them, generating a vaccine whose active principle is the nucleic acid molecule, constituted in addition by a carrier.—US200423580 discloses that in the formulation collaborating molecules take part; the kit of diagnosis is also claimed. The present application, besides the differences in the sequences, transfer and formulation, presents differences with reference to the process and the route of administration.

US2004146860, WO03/035680, CA2321437, WO01166569, WO0149712 and US69119083 are vaccines against ISAV virus. All of them indicate the same intention that is the protection of a sequence, either peptide or nucleotide, as active principle of the pharmaceutical formulation. All the formulations are based on the sequence that it codifies for a polypeptide that is united to an antibody obtained from an animal infected with ISAV. The diagnosis kit is also claimed in some documents of the prior art. The present application presents deep differences. The first great difference is the active-ingredient, since the sequences are different and distinctive, because they are of a different virus like IPNV virus, besides the differences in the sequences that appears in the recombinant plasmid and the cession carried out through a cationic liposome, differences that define a new pharmaceutical composition. There remain the great differences with the cession process that includes the oral route in a nutritional formulation.

KR2003078807, CA2407301 and CA2381708 propose a vaccine against *Piscirickettsia salmonis*. Likewise the set of previous documents of the prior art grouped in this part are only related to the present application because all are fish vaccines, whose active substance is of hybrid or molecular nature, formulations that generate an immune response by the cession of nucleotide or polypeptide sequences after the fish vaccination. The differences with the present application are large, the compositions are discordant. In the donation stage they are different vectors that take part, the cession is done by other routes and other agents take part. In summary, no formulations for DNA vaccines against virus IPNV have been found that are similar to the composition that is desired to claim in the present application.

WO2003/101482 A3 discloses the formulation of a fish vaccine including the antigenic material derived from one or more pathogenic fish in association with liposome, and optionally includes other therapeutic compounds. The vaccine can be used to immunize or for therapeutic treatments against the pathogens of this fish. The invention also claims the preparation method, administration and storage of the liposomal vaccine.

Even though WO2003/101482 A3 claims the liposome used to generate a vaccine against IPNV, the described sequences do not have report, like either the primers or the expressed peptide sequence. A composition must be claimed by its components, but in the world petition it does not establish what part from it is specifically DOTAP cationic liposome. In addition, the claimed composition has a specific use for a determined fish species, different from which is desired to protect in the present application. The pharmaceutical composition in WO2003/101482 A3 is composed by the active ingredient that can be a nucleotide sequence of IPNV virus, a "liposome". But without describing which of the existing ones, one or more lipid classes are indicated ambiguously, one or more bioactive, one or more adjuvant agents, bioactive agents, and "pharmaceutically acceptable" carrier. This is that the composition that is desired to claim has no report with WO2003/101482 A3, although tangentially it seems related. In addition, the manufacture process is clearly different and the world petition does not explain either how the active principle is going to be yielded to the fish. What WO2003/101482 A3 establishes is that the product is the result from the formulation with liposome. Nevertheless, in the present application the product is a nutritional formulation that contains a vaccine, specifically for the virus of the infectious pancreatic necrosis. The same technology can be used for other pathogens.

6. Search of documents related to the preparation of a nutritional formulation for fish that contains a DNA vaccine:

No documents were found in the prior art under this search criterion.

SUMMARY OF THE INVENTION

The present application seeks to provide a DNA vaccine for fish, incorporated into a fish feed, the vaccine comprising: (a) a plasmid construct pcDNA-VP2 carrying a fragment of 724 bp, according to SEQ ID NO:3, (b) a DOTAP liposome, and (c) an excipient having nutritional properties.

The present application also seeks to provide a process for obtaining a DNA vaccine for fish, incorporated into a fish feed, the process comprising the following steps: (I) synthesizing a primer construct with the primer of FIG. 1; (II) forming a plasmid construct pcDNA containing SEQ ID NO.: 5; (III) transferring, cloning and purifying a pcDNA-VP2, (IV) forming a complex containing a carrying plasmid of a fragment of SEQ ID NO.:5 of virus IPNV and a DOTAP liposome, generating a lipoplex; (V) dispersing, mixing and integrating the lipoplex to a nutritional composition comprising an oral vaccine or a formulated vaccine, and (VI) packaging the nutritional composition containing the DNA vaccine.

The present application also seeks to provide a pharmaceutical composition containing a DNA fish vaccine, the DNA vaccine for fish comprising: (1) an active principle derived from the use of the primers of FIG. 1 with the sequence of SEQ ID NO. 5; (2) a DOTAP cationic liposome as a vehicle, and (3) nutritional, innocuous and pharmaceutically acceptable excipients, the excipients being nutritional and digestible by fish.

The present application also seeks to provide a nutritional composition, comprising: crude protein in an amount ranging from 450 g/Kg to 600 g/Kg; lipids in an amount ranging from 150 g/Kg to 250 g/Kg; ashes in an amount ranging from 80 g/Kg to 120 g/Kg; crude fiber in an amount ranging from 6 g/Kg to 10 g/Kg, and nonnitrogen extract in an amount ranging from 70 g/Kg to 80 g/Kg.

BRIEF DESCRIPTION OF THE DRAWINGS

FIG. 1 shows the primers used, which are SEQ ID NO:1, SEQ ID NO:2, SEQ ID NO:3, and SEQ ID NO: 4, respectively.

FIG. 2 shows the scheme of amplification of the immunogenic sequence from RNA viral.

FIG. 3 shows SEQ ID NO: 5, which is a sequence of 724 bp from the capsid protein VP2 of the Infectious Pancreatic Necrosis virus (IPNV, cloned in the pcDNA4/HisMax-TOPO (TRADEMARK), run into plasmid Sequencing in the Biotechnology Center of the Faculty of Sciences of the University of Chile.

FIG. 4 shows details of the region of multiclonation of the vector pdDNA4/HisMaxTOPO (TRADEMARK).

FIG. 5 shows the amplification of insert from plasmid pcDNA-VP2 isolated from cellular cultures transferred.

FIG. 6 shows the results of the evaluation of structural stability of the plasmid vaccine.

FIGS. 7 and 8 show the incorporation process of the vaccine into the food

DETAILED DESCRIPTION OF THE INVENTION

The present application seeks to protect a process and a product. The process allows formulating a developed veterinary pharmaceutical composition through techniques of molecular Biology, which consists of a type of DNA vaccine against pathogenic virus to be included in the food of organisms in culture systems. The product to protect is the pharmaceutical composition above-mentioned, whose main characteristic is that it can be administered in oral form—without manipulation of each individual—to animals that are in massive production systems.

The work accomplished in this application was more specifically in fishery systems and on fish pathogens. The application looks to claim a process for the manufacture of a DNA vaccine in front of a viral pathogen. This vaccine is applied in fish, particularly salmon group, and is conceived for fishery centers. The application consists of several stages that go from the isolation of a codifying genetic sequence of viral polypeptide component to the industrial scaling process. The process consists in the execution of this formulation with a palatable excipient, so that the individuals eagerly ingest the food that contains a vaccine, which is absorbed in enteric form by fish and have pharmacological action in different tissues of the fish.

The formulation to be protected is conceived to be administered in oral form, being part of the food the pharmaceutical formulation, whose active ingredient is the genetic sequence of interest, which is contained in a plasmid that is complex by a liposome as well.

The application is foreseen to claim a process that can be applied to the food manufacture that contains vaccines to immunize any type of organisms. In this case, it was applied to the fishery industry, but it can be a process applicable to the industry of bird-raising, pig, horse, goat, among others. Following the application is described.

Production of Virus, Proteins and Primers.

The virus of the Infectious Pancreatic Necrosis (IPNv) is a virus of the Birnaviridae family whose genome is bisected, of double chain of RNA, where the smaller sub-genomic segment (segment B) codifies for an enzyme RNA-dependent-RNA polymerase (VP1), whereas the bigger segment (segment A) codifies polyprotein NH2-VP2-VP4-VP3-COO—, where VP2 and VP3 are structural proteins and VP4 a viral protease in charge of the auto process by proteolysis by means of which precursory intermediaries are sequentially generated and then originate the functional mature components. These are VP2 that are totally exposed or partially in the most external layer of the viral capside; VP3, that is the one that interacts with VP1, reason why we think that it is in the intern face of the capside; and VP4, the protease responsible for the auto process (Duncan and Dobos, 1986; Duncan et al. 1991).

The first step is the obtaining of the genetic matter of the pathogen, in this case RNA or DNA. The RNA is necessary for the amplification of the sequences that they codify for the segment of a protein with proven immunogenic activity. In the case of IPNV virus that attacks salmon group, a complementary codifying DNA was of a region of the subunit "A" of protein VP2. For this, confluent unilayers of embryonic cells of salmon Chinook CHSE-214 (ATCC 1681) infected with IPN Passed a period of postinfection, the total RNA was extracted using Trizol (Invitrogen TRADEMARK). In order to isolate the RNA viral of the cells, a kit QIAamp (Qiagen TRADEMARK) was applied, obtaining in pure form the viral RNA.

Figure 1:
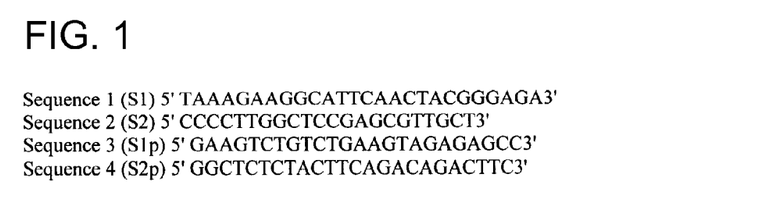

The second step is the obtaining of the amplified nucleotide sequence. For this, after the codifying genetic sequence has been defined of the viral protein that contains the antigenic region of interest, the primers of RNA were constructed in first instance and later the complementary DNA (cDNA), everything through an inverse polymerase reaction and chain reaction of polymerase. The primers used can be seen in FIG. 1. These allowed amplifying and cloning in a selective form the information that codifies in particular for epitope of sub-unit two of the protein of capside of IPN virus. In the particular case of IPN virus, the amplified nucleotide sequence was of the segment "A" of IPNV, whose origin is around 250 bp from the terminal amino end. For this study a bioinformatics analysis of sequences of the following serotypes was considered: Vr299, Ja-ATCC, C2, Ab, ASV, Sp and He, corresponding to the six geno-groups described for this virus. The Vr299 serotype was taken as a reference given its prevalence in Chile. The alignment analysis and homology were made through the data base of Gene Bank and a program of alignment of nucleotide sequences (BLAST or DNAman). The analysis showed a homology of the amplified sequence of the viral genome superior to 85% in relation to the rest of the IPNV serotypes.

A protocol was adapted to carry out the reverse amplification (RT-PCR) from the total and viral RNA. The cDNA of the viral genomic region of interest is used as tempering for the later amplification for PCR. Two antisense primers S2 and S2p were evaluated, designed to hybridization with a specific sequence of the subunit A of the IPN virus and generating the complementary DNA fiber.

Figure 2:
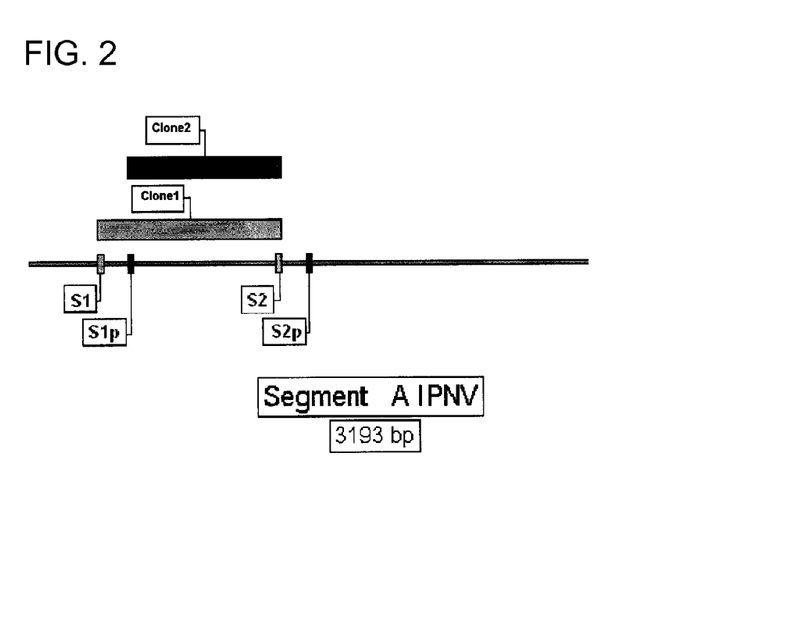

Once obtained the cDNA, the sequence with different combinations of primers was amplified: FIG. 2 shows the scheme of amplification of the immunogenic sequence from viral RNA, which was amplified with the following primers:

| Sense: | S1 S1p | Fragment of 608pb (primers S1p and S2p) |
|---|---|---|
| Antisense: | S2 S2p | Fragment of 724pb (primers S1 and S2) |

| Combination | Size of amplicon (pb) |
|---|---|
| S1p and S2 | 608 |
| S1 and S2 | 724 |

The fragments obtained by PCR were visualized in gels of agarose and quantified by spectrophotometry. Later, the procedure to purify was accomplished by precipitation with ethanol the amplicons of 608 and 724 bp.

Figure 3:
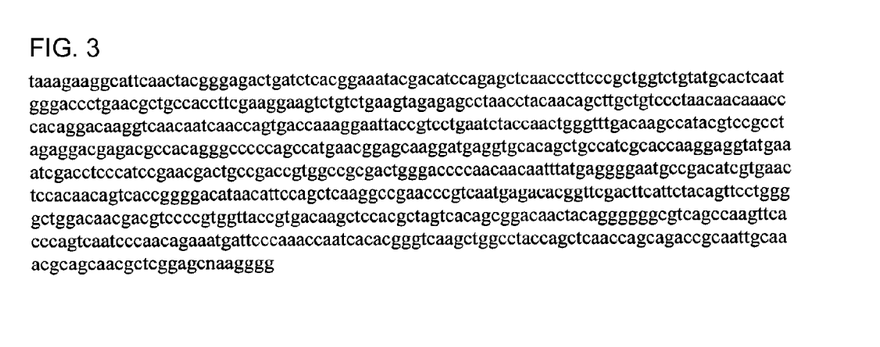

FIG. 3 shows the sequence of codifying genomic region of 724 bp of the immunogenic viral peptide of protein VP2 of IPNV generated for this initiative, whose sequencing was carried out in the Center of Biotechnology of the Faculty of Sciences of the Universidad de Chile.

The third step of the process is the formation of plasmid construct and insertion to the expression vector. The vector of expression of mammals pcDNA4/HisMax TOPO allows the insertion of the amplification product with high efficiency. The viral promoter used is the cytomegalovirus (CMV) and a potential of the translation, the one that was used to obtain a high rank of expression. With the purpose of detecting and purifying the polypeptide generated from PCR products, this polypeptide is expressed next to the end N-terminal of Xpress (TRADEMARK) and to the rest of histidine (Invitrogen TRADEMARK Life Technologies TRADEMARK).

Figure 4:
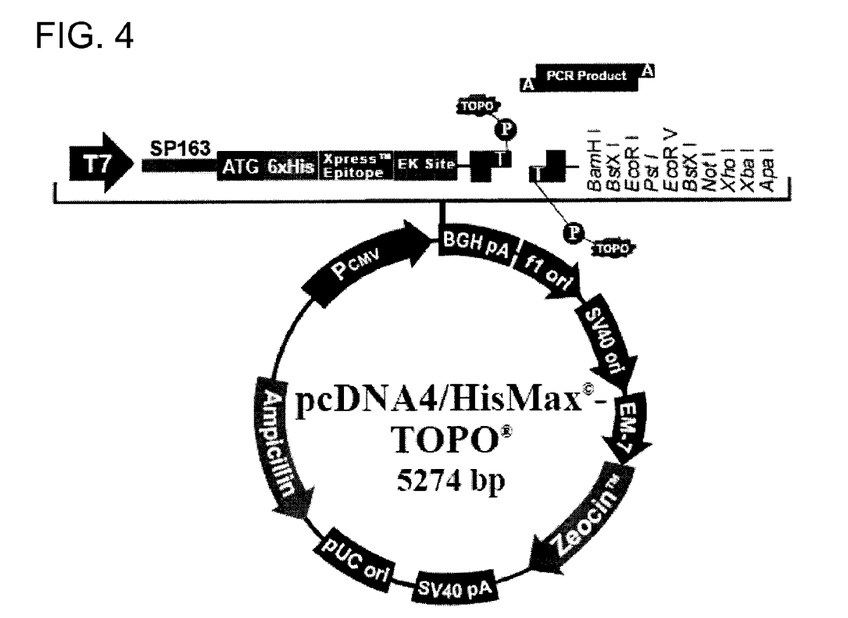

The plasmid construct includes the sequence coder for the polypeptide desired, which is hosted in the plasmid pcDNA4/HisMaxTOPO (TRADEMARK). This construct is named pcDNA-VP2. In order to amplify this vector the bacterial stock *Escherichia coli* JM-109 was used, which was transformed with amounts known of insert of interest. The bacterial clones that own the plasmid were isolated, after propagation of the recombinant stock in liquid cultures applying selective pressure (kanamicina and ampicilline). The insertion of the gene was confirmed and its correct orientation in the plasmid after comparing the patrons of cuts generated by the of restriction Pvu II, with the insert and without it, and when extending with specific primers of the plasmid pcDNA4/HisMaxTOPO (TRADEMARK) the region of multiple cloning. In FIG. 4 shows in detail the region of multiclonation of the vector pdDNA4/HisMaxTOPO (TRADEMARK).

The presence of colonies of bacteria *E. coli* JM-109 in culture with selection pressure indicates the receiving stocks of genetic material. In order to assure the maintenance of the transformed bacterium, these were cultivated in a reactor, in Luria Bertani, for 4 hours and soon they were stored in glycerol −80° C.

The purification of the plasmid was accomplished after the culture of the bacterium. For laboratory analysis the kit "Quantum prep. Plasmid Miniprep" of Biorad (TRADEMARK) was used. For the scaling the kit "QIAGEN (TRADEMARK) Plasmid Mega" was used, which allows the purification of plasmid from volumes above 500 ml of bacterial cultures.

In order to determine if the fish cells are able to incorporate the clone plasmid pcDNA-VP2 and if in conditions of expressing the insert of the portion of viral protein VP2 of IPNV virus, the unilayers were transferred subconfluents CHSE-214, after which extractions of plasmid DNA and RNA total with Trizol on different times from postranafection were accomplished.

Figure 5:
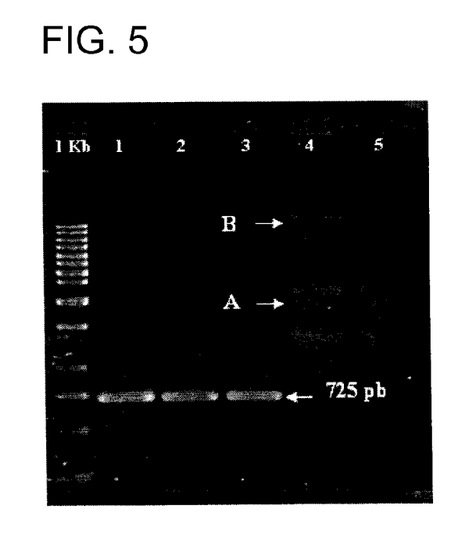

From the isolated plasmid DNA it was accomplished the PCR to obtain the amplified product defined according to the pair of selected primers. The presence of amplicons of 724 bp in gels of agarose at 1% indicated that the cellular line was able incorporate the plasmid with the insert. Of RNA extracted of the total of the cellular culture RT-PCR some analysis were accomplished to amplify from messenger RNA present in the sample, the sequence of VP2 of IPNV, as shown in FIG. 5, which agarose gel that verifies the viral insert amplification from the plasmid pcDNA-VP2 from cellular culture transferred. FIG. 5 shows the amplification of insert from pcDNA-VP2 isolated from cellular cultures transferred. The plasmid DNA and the messenger RNA were extracted from cells CHSE-214 (track 4 and 5). Fragments of 724 bp were obtained (tack 1, 2 and 3) amplified by PCR from the plasmid vector. 0 corresponds to the marker of molecular weight; in "A" is the point of migration of the total RNA of the sample and in "B" the plasmid. It is possible to verify that after digesting with restriction enzymes a nucleotide fragment is obtained, which is of similar length to the expected one. Also, the obtaining of the plasmid demonstrates incorporation of this in the cellular line.

Selection of Vehicle.

The present application discloses a bacterial cellular new line that contains a vector consisting of induced expression consistent with the plasmid constructed genetically. This line corresponds to stock *E. coli* JM-109, which was transformed with the plasmid that is on FIG. 4, plus the insert shown on FIG. 3 constituting the recombinant stock *Escherchia coli* JM-109 (pcDNA-VP2). The obtained recombinant plasmid contains the necessary information for the synthesis of the interest polypeptide, that is part of subunit 2 of the protein capside of IPNV virus. After the transformation, the bacterium incorporates the vector and is able to amplify this genetic component. When this plasmid construct (pcDNA-VP2) is administered by oral route, in a determined formulation, will generate an immune response in the white organism, specifically in the fish. The plasmid also presents a marking gene of ampicilline. Recombinant stock *E. coli* JM-109 (pcDNA-VP2) was deposited in Belgian Coordinated Collection of Microorganisms (BCCM), whose accession number is LMBP 5333.

An important aspect of this application is that the plasmid, after being cloned is isolated and complex to a cationic liposome (DOTAP), generating a complex denominated "Lipoplex". The Lipoplex induces the synthesis of immunogloblobulin by itself, although this is a stage of the application.

The present application, through the use of DOTAP liposome, secures a non direct procedure of transformation, where the morning cells express the polypeptide codified by the plasmid with a high rate of transfection.

In relation to the DNA quantification contained in the complex "lipoplex", it is possible to indicate that the samples of lipoplex, in report DNA: DOTAP 1:4, were put under centrifugalization and later resuspension in water, to be then loaded in agarose gels. The estimation of the DNA merger was accomplished by means of analysis densitometer. To the left hand side the marker of molecular weight.

Track 1: Plasmid DNA 42 ng in MEM.
Track 2: Resuspension of the plasmid extract subsequent to the treatment with MEM and centrifugalization.
Track 3: Lipoplex 42 ng of plasmid in MEM.
Track 4: resuspension in MEM subsequent to the centrifugalization of Lipoplex.
Track 5: DOTAP to 170 ng in MEM.
Track 6: Only MEM.

Lipoplex by itself can induce an immune response, as DNA vector that is complex or encapsulated in a cationic liposome (DOTAP). The vaccine is introduced to the food, this means that the nucleotide sequence of IPN virus is carried out by the plasmid and formulated with the food base of fish. The food is digested in the digestive tract and the vaccine is released in the intestine of the individual. The pharmaceutical composition (liposome-DNA) generates the therapeutic answer required. This answer is the result of the cellular incorporation of the viral genetic sequence, which will generate the expression of the viral peptide. The cell, when exhibiting a polypeptide sequence unknown by the guest, will induce the immune response and, therefore, the protection to the infection by the agent who contains the sequence in his surface or capside viral.

FIG. 6 presents the results of the evaluation of structural stability of the plasmid vaccine. Cellular cultures of CHSE-214 according to the conditions optimized experimentally were transferred and the plasmid and the messenger RNA (a) were prosecuted at 6, 12, 24 hours, obtaining the plasmid and RNA messenger (a). From the messenger RNA it was amplified by RT-PCR the insert of 724 bp of IPNV(b).

The administration of this vaccine, particularly to fish, in the form of food, supposes also to facilitate the vaccination process and the possibility of selecting the optimal stage of vaccination following the species of fish in culture. It can be determined the stage when the fishes are more susceptible to the pathogen, or it is possible to induce the answer and effective resistance on the base of the kinetic behavior and of each affection in a certain species of culture.

The application further has ecological benefits, since applying an efficient alternative of eradication of introduced pathogenic agents contributes to mitigate the indiscriminate antibiotic used with demonstrate adverse effect on the environmental microfauna.

Description of the Process for the Manufacture of the Food Base.

1) Formulation, Dosage and Mixture:

The experimental results determined as condition the incorporation of the Lipoplex more specifically to an aqueous solution that must be in a range between 0% and 50% more specifically 0% to 25% weight of food. The use of spray as aspersion element was defined in addition to reach the homogenous covering of food particles.

The chain of the process is intended for any type of productive process that generates food for centers of animal production. Nevertheless, in the present application is only disclosed the process related to food manufacture, whose form of administration is a pellet, reason why it will be generic.

The raw materials with which the base food is formulated are ground on the first stage. The sorting is previously determined on the basis of environmental norm and international standards.

The process that originates the finished product is initiated with the diet formulation. Each one of the ingredients that compose the specific diet of the animal are dosed, through batch operations of components of the mixture, in powder and oiling batch. The amounts of pellets that must be dosed with liquid products are programmed in the batch, as well as the special ingredients that can be dosed through liquid ingredients, such as specific vaccines, depending on the white organism.

In the stages of dosage and mixture, the ingredients and additives are weighted and mixed, obtaining a suitable proportionality and homogenization of the dry powder components of the diet.

2) Extrusion.

In this stage the ingredients mixed with water, oil and/or additives through oil and pressure are prepared already. The pressure is exerted by an endless screw in the barrel of the extrusor. There is a layer or matrix perforated, which is located at the end of the barrel. This will allow formation of a cylindrical form, plus two spherical units. This stage allows giving a final form to the micro-pellets with rounded edges similar to those of the microcapsule. The humid extrusion allows the partial gelatinizing of the carbohydrates, as well as the texturization of the proteins from the different ingredients of the diet. This way, it is possible to obtain the consistency and the agglutination of pellet bases, with the form and physical appearance required for each type of product.

3) Description of the Addition Method of the Lipoplex in the Food Bases.

As it has already been indicated, the food bases are the vehicle to add the Lipoplex complex, whose process of addition can be accomplished through two mechanisms: 1. Vacuum dispersion, and 2.—Simple dispersion Vacuum Dispersion:

The incorporation process of the vaccine to the food is developed in a batch process with two routes of feeding: (a) a dry route and a (b) liquid route.

The dry route (a) consists of dosing in a weight a predefined amount of food bases in the form of pellets, which are spilled to an oil-mixer with vacuum. When applying vacuum it is allowed to generate inside the oiler a pressure lower than the atmospheric pressure, so that when depressurizing the air is forced to leave from the free space of the oiler as well as from the interior of the pellets along with part of the oleic of the oil of lower fusion point already present in the food.

The liquid route (b) operates in parallel and in two stages. It has two deposits maintaining in one of them pre-dosed lipoplex according to the caliber and the of food base that was programmed in the oiling batch. In the first stage the vaccine is added by means of a fine aspersion under vacuum conditions and mixture to assure a suitable impregnating of all the pellets. Next, the vacuum is freed slowly allowing the air entrance, so that it is possible to return to the atmospheric pressure, facilitating that the vaccine that is initially in the surface with part of the free oil is pushed by the air towards the interior of the pellets. Secondly, under normal atmospheric pressure, the fish oil that has been pre-weighted in the second deposit is also applied finely by aspersion under mixture conditions dragging with itself any vaccine surplus that could have been in piping. This process is called top coating and allows covering all the surface of each one of the pellets minimizing the direct exposure of the active in the food surface.

Once the vaccine is incorporated in the food and covered with oil, the oiler-mixer equipment turns in 180° to position itself in the entrance mouth of the pre-bagging hopper. Once the oiler-mixer is positioned in the unloading, the butterfly valve of the equipment is opened leaving to fall by gravity all the batch preparation to the hopper that feeds directly the weigh equipment and package. More details of the process can be seen in FIGS. 7 and 8.

Simple Dispersion:

This second option of the incorporation of the vaccine to the food, like the previous one, is developed by two routes of feeding: a dry route (a) and a liquid route (b).

The dry route (a) consists of classifying in a weigh a predefined amount of food bases in the form of pellets which are incorporated to a mixer rotating boiler type of angle and variable speed. This system allows, on the basis of the rotation, to obtain uniform mixing of the pellet food. The number of revolutions must graduate between 5 and 50 rpm and the position angle with respect to the horizontal between 10° and 35° to obtain a homogenous mixed cycle. Then, the liquid route takes place.

The liquid route (b) operates altogether with the mixer and only consists of a sprinkler connected to a dispenser, which is preprogrammed according to the caliber and amount of food bases. The impregnating that takes place is instantaneous, since the sphere food is highly hygroscopic, reason why it will efficiently absorb the liquid sprinkled by the sprinkler. Once incorporated the vaccine to the food bases by means of the sprinklers, the mixer turns in 180° to be located in the entrance base of the pre-bagging hopper. A spill valve will allow dropping by gravity the total batch preparation to the hopper that feeds directly the weigh and package equipment.

Drying and Cooling.

It is a physical process that allows fitting the amount of water required for the final product. Then, the product is cooled, avoiding risks associated to microbiological degradation of high temperatures. The process finishes with the packaging, whose object is to pack the product according to engineering specifications.

Packaging.

The process finishes with the packaging, whose object is to pack the product according to a series of specifications.

The food bases for different organisms which are considered to transport the oral vaccine appear in several sizes and nutritional composition in accordance with their requirements and the stage of productive cycle in which they are at the time of making the treatment.

The present application solves several problems of the technique, such as the massive vaccination of individuals. In this case of young fishes avoiding its manipulation, with the stress that it implies, as well as operational benefits related to the easy administration of the oral vaccine, high stability and simple storage.

Examples of Process

A. Evaluation of the Capacity "In Vitro" Expression of the Gene Insert VP2

The unilayers CHSE-214 cells were cultured to 80% of subconfluence. The cells were worked in the MEM area, sodium bicarbonate 2.2 g/L and fetal vaccine serum (SBF) to 2.5%, to a temperature of 20° C. per period of 4 to 14 days in plates of twelve smalls cups. Soon the cells were washed with prepared PBS and for the incorporation of plasmid construct (pcDNA-VP2) complex with liposome DOTAP.

As previously discussed, they were added in aliquot of DNA and DOTAP in MEM area. Next they were mixed and were incubated by 30 minutes. The transfer was accomplished adding each mixture to a total volume of 0.5 ml of MEM on cellular unilayers. Once the time of incubation fixed for the transfer (MEM more SFB 5%) passed, the extraction of plasmid took place.

The plasmid extraction from cellular line CHSE-214 was accomplished according to the protocol described for Trizol (Invitrogen TRADEMARK Life Technologies), which considers in general terms the retirement of the MEM area with bovine fetal serum 5%, washed of the cells with PBS, addition of a reagent volume, incubation for 5 minutes at room temperature, chloroform addition and later centrifugalization to 12000 g for fifteen minutes. Of the two formed phases, the superior watery phase contains RNA and the plasmid, while the inferior phase contains genomic DNA.

The extracted plasmid was precipitated with isopropyl alcohol, centrifuging them and washing themselves with ethanol at 70%. Finally, the solvent evaporated the desionized sterile water sample was re-suspended. The plasmid DNA sample was loaded in a gel of agarose at 1%, dyed with ethidium bromide (0.5 μg/ml) and visualized in translighter at 260 nm. The migration profiles in the gel revealed the integrity of the plasmid. The densitometers analysis indicated for different studied times 11, 65; 13, 65 and 461 ng of plasmid vaccine, respectively. As additional test the fragment was amplified at 724 bp from the mRNA by means of RT-PCR, obtaining itself the product of amplification desired (724 b) in the three times of evaluation.

Process Example and Food Formulation.

Pellet food for salmons of culture in fresh water was formulated, whose results appear below.

The detail of the composition of these food bases as well as their use recommendation is indicated in Table 1. The use recommendations are described in Table 2.

TABLE 1

Food bases required to transport the oral vaccine.

| Caliber | 2 | 5 | 15 | 50 |
|---|---|---|---|---|
| Composition, average (g/kg) | | | | |
| Crude protein | 530 | 530 | 500 | 500 |
| Lipids (analyzed by acid hydrolysis) | 200 | 200 | 220 | 220 |
| Humidity | 85 | 85 | 90 | 90 |
| Ashes | 100 | 100 | 95 | 95 |

TABLE 1-continued

Food bases required to transport the oral vaccine.

| Caliber | 2 | 5 | 15 | 50 |
|---|---|---|---|---|
| Crude fiber | 8 | 8 | 10 | 10 |
| NonNitrogen extract | 77 | 77 | 85 | 85 |
| Energy, MJ/kg | | | | |
| Gross energy | 21.92 | 21.92 | 22.35 | 22.35 |

Ingredients Selected in the Formulation:

Fish flour, fish oil and/or vegetal oil, flour milling of wheat and maize by-products, concentrate of peptones, gluten of wheat and maize, krill flour, premixtures of vitamins and salts, minerals, soy protein concentrate, wheat, betaine and nucleotides.

TABLE 2

Food use recommendations.
Therapeutic dose.

| Size of the Food | Size of the fish in grams |
|---|---|
| 2 | 2-7 |
| 5 | 7-15 |
| 15 | 15-50 |
| 50 | 50-100 |

The therapeutic dose is based on the fish rate of feeding (SFR), that express themselves as well as % in weight of the biomass to be treated. Plasmid concentrations in the food have been determined on the basis of a pre-established SFR, so that the vaccine is administered homogenously with a unique dose in the food according to caliber. This way, it is assured a dose delivery that covers the minimum injunction with plasmids under conditions of a low SFR. If during the food administration with vaccine the fish presents more SFR than the pre-established one, the amount of food is adjusted providing food with and without vaccine. The vaccine dose and SFR for the different food calibers is detailed in Table 3.

TABLE 3

Therapeutic dose based on Rate of Pre-established Feeding.

| Food with Vaccine | | | | Therapeutic dose | |
|---|---|---|---|---|---|
| Food Caliber | SFR % | Concentration mg plasmid/ Kg | Duration Treatment Days | Per Day mg plasmid/ Kg Fish | Per Treatment mg plasmid/ Kg |
| 2 | 2.00 | 100 | 5 | 2 | 10 |
| 5 | 1.60 | 125 | 5 | 2 | 10 |
| 15 | 1.25 | 160 | 5 | 2 | 10 |
| 50 | 1.00 | 200 | 5 | 2 | 10 |

Table 4 contains the size specifications for spherical micropellets, and Table 5 contains similar specifications for cylindrical pellets.

TABLE 4

Size specifications for spherical micropellets.

| | Micropellets Spherical | | | | | |
|---|---|---|---|---|---|---|
| | Diameter | | | Length | | |
| Caliber | Min. mm | Target Mm | Max. mm | Min. mm | Target mm | Max. mm |
| 2 | 1.00 | 1.10 | 1.30 | 1.35 | 1.70 | 1.90 |

TABLE 5

Size specifications for cylindrical pellets.

| | Cylindrical Pellets | | | | | |
|---|---|---|---|---|---|---|
| | Diameter | | | Length | | |
| Caliber | Min. mm | Target Mm | Max. mm | Min. mm | Target mm | Max. mm |
| 5 | 1.4 | 1.6 | 1.7 | 1.4 | 1.6 | 1.7 |
| 15 | 1.5 | 1.7 | 1.9 | 2.9 | 3.2 | 3.5 |
| 50 | 2.0 | 2.2 | 2.4 | 3.5 | 3.8 | 4.1 |

Evaluation Examples of the Vaccine Immunogenetic Potential:

An experiment was accomplished to determine the effectiveness of the vaccine formulated in the food bases. The administration of the oral vaccine was sufficient to generate the immune response in fish tested, whose resistance to the pathogenic stock was verified in challenge bio-tests.

A total of 5000 young fish (*Salmon salar*) were immunized of 5 g through the ingestion of oral vaccine. The dosage scheme included the elaboration of a master food, which was diluted to reach the different levels wished with the food.

The live analysis was developed with separate young fishes by pools according to dose and controls. The young fishes were fed during 7 days with the vacunal dose. Then, samples were obtained for times of 0, 15, 45, 60 days post feeding with vaccine. The vaccine Alphajet 1000 (TRADEMARK) of Allpharma (TRADEMARK) was selected as a positive control administering itself by intraperitoneal route to a group of young fishes after passing 45 days that the experience was initiated.

Kinetic expression of the gene reported was studied through obtaining blood samples during 0, 15 and 45 days after initiated the experimental analysis. The ELISA analysis allowed determining the estimation of the immune response, where the estimation of the immune response before the antigenic heterologous protein in order find the antibody against IPNV in plasma sample of immunized fish with the plasmid vaccine was determined.

The analysis considered the accomplishment of an indirect ELISA, for detecting the level of total antibodies by means of the reading of absorbance to 450 nm of the product generated by the reaction of TMB (Tetrametilbenzidina) in the presence of $H_2O_2$ and peroxides. 96 smalls cups dilutions series were covered with plasma (1, 1:2, 1:4, 1:16) incubated for 4 h. at 15° C., after washing with PBS/Twenn 20 0.05%. Blockade with PBS/Tween 20 0.05% plus 5% of skimmed milk 1 h at room temperature. Again it was washed and it was incubated with dilutions of Ab anti Salmon (1:100, 1:200, 1:400, 1:800, 1:1600) in PBT/Tween 20 0.05% for 2 hours at room temperature.

Later a dilution was added of 1:3000 goat antibodies anti IgG of mouse conjugated with peroxides in PBS/Tween 20 0.05% for one hour at room temperature.

Finally, a dilution was added of 1:3000 goat antibody anti IgG of mouse conjugated with peroxides in PBS/Tween 20 0.05% two hours at room temperature. After washing TMB was added waiting 20 minutes at room temperature to observe a coloration. The reaction was stopped with $H_2SO_4$ 1N and the product generated was quantified by a reader for ELISA plates by absorbance reading of 450 nm.

For the detection of specific antibodies multi small cups plates were incubated with virus IPN 1*105 UFP/ml, then plasma in pre-established dilution (1:16) was added and-subsequently carry out each one of the described steps to determine indirectly this molecule class. The results obtained for the dose 1 mg/Kg PV indicated statistically significant differences with an interval of 90% between the control and the fish fed with the plasmid vaccine 45 days of administered the nutritional formulation that contained the plasmid vaccine.

The invention claimed is:

1. A DNA vaccine for fish, incorporated into a fish food comprising:

a. a plasmid construct pcDNA-VP2 comprising a 724 bp insert as set forth in SEQ ID NO: 5;

b. a DOTAP Liposome; and c. a nutritional food base.

2. The DNA vaccine of claim 1 wherein the nutritional food base comprises a. Crude protein in an amount ranging from 450 g/Kg to 600 g/Kg;

b. Lipids in an amount ranging from 150 g/Kg to 250 g/Kg;

c. Ashes in an amount ranging from 80 g/Kg to 120 g/Kg;

d. Crude fiber in an amount ranging from 6 g/Kg to 10 g/Kg; and e. Nonnitrogen extract in an amount ranging from 70 g/Kg to 80 g/Kg.

3. The DNA vaccine of claim 1, wherein the nutritional food base comprises:
   a. fish flour,
   b. fish oil and/or vegetable oil,
   c. by-products of wheat and maize,
   d. peptone concentrate,
   e. gluten of wheat and maize,
   f. krill flour,
   g. premixtures of vitamins and mineral salts,
   h. soya mineral salts,
   i. wheat,
   j. betaine, and
   k. nucleotides.

4. A process for obtaining a DNA vaccine for fish, incorporated into fish food, comprising:
   a. constructing a plasmid pcDNA-VP2 comprising SEQ ID NO: 5;
   b. transforming a suitable stock host cell with pcDNA-VP2;
   c. amplifying and purifying the pcDNA-VP2 from the stock host cell;
   d. forming a lipoplex that is a binary complex comprising pcDNA-VP2 and a DOTAP liposome, thereby generating a lipoplex;
   e. dispersing, mixing, and integrating the lipoplex into a nutritional food base to make an oral DNA vaccine or a formulated DNA vaccine; and
   f. packaging the oral or formulated DNA vaccine.

5. The process of claim 4 wherein the suitable stock host cell used is a strain of *E. coli* 1M-109 deposited at the Belgian Coordinated Collection of Microorganisms (BCCM) under the Accession No. LMBP 5333.

6. The process of claim 4 wherein amplifying and purifying pcDNA-VP2 from the stock host cell is done through an alkaline lysis process comprising sequential stages of centrifugation, filtration and ultra filtration.

7. The process of claim 4 wherein dispersing, mixing, and integrating the lipoplex into a nutritional food base to make an oral DNA vaccine or a formulated DNA vaccine is done through a pan coating system.

8. The process of claim 4 wherein dispersing, mixing, and integrating the lipoplex into a nutritional food base to make an oral DNA vaccine or formulated DNA vaccine is done by way of dry inlet with pre-oiled feed under vacuum conditions.

9. The process of claim 4 wherein dispersing, mixing, and integrating the lipoplex into a nutritional food base to make an oral DNA vaccine or formulated DNA vaccine is done in by way of liquid inlet, under vacuum conditions.

10. The process of claim 9, wherein the lipoplex is added through the liquid inlet in parallel and in stages; wherein in the first stage, the lipoplex is added by means of a fine dispersion under vacuum conditions, and in the second stage pre-weighed fish oil is dispersed under normal atmospheric pressure.

11. The process of claim 8, wherein the lipoplex is added to a predefined amount of food base and is incorporated in a rotating mixer.

12. A pharmaceutical composition comprising a DNA fish vaccine comprising:
    (a) a plasmid comprising the sequence of SEQ ID NO: 5;
    (b) a cationic DOTAP liposome as a vehicle; and
    (c) nutritional, innocuous, and pharmaceutically acceptable excipients, wherein the excipients are nutritional and digestible for fish.

13. The pharmaceutical composition of claim 12 wherein the DNA vaccine is prepared for oral administration.

14. The pharmaceutical composition of claim 12 wherein the DNA vaccine is prepared as pellets for oral administration.

15. The pharmaceutical composition of claim 12, wherein the composition is useful for immunizing fish.

16. The pharmaceutical composition of claim 12 wherein the pharmaceutical composition is useful for immunizing fish against a virus of infectious pancreatic necrosis and for nourishing the fish.

\* \* \* \* \*